United States Patent [19]
Januzeli et al.

[11] Patent Number: 6,098,796
[45] Date of Patent: *Aug. 8, 2000

[54] SURGICAL SUTURES DISPENSER AND A METHOD OF COILING SURGICAL SUTURES

[75] Inventors: Jose Lucio Leite Januzeli; Marcos Andre Bordigon, both of Sao Jose dos Campos-SP, Brazil

[73] Assignee: Ethicon, Inc., Somerville, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 09/086,244

[22] Filed: May 28, 1998

[30] Foreign Application Priority Data

Jun. 10, 1997 [BR] Brazil ..................................... 9703513

[51] Int. Cl.[7] .................................................. B65D 85/00
[52] U.S. Cl. ......................... 206/227; 206/63.3; 206/380
[58] Field of Search .................. 206/63.3, 227, 206/380, 490

[56] References Cited

U.S. PATENT DOCUMENTS 4,258,843  3/1981  Wymer ................................... 206/63.3
5,675,961  10/1997  Cerwin et al. ......................... 206/63.3

*Primary Examiner*—Jim Foster
*Attorney, Agent, or Firm*—Emil Richard Skula

[57] ABSTRACT

The present invention refers to a surgical suture dispenser (1) especially suitable for retaining prepared sutures (4,5), that is to say, sutures provided with one or more needles (5), which are coiled in the dispenser (1) so that the respective needle (s) can be accessible through its central portion. This invention also relates to a method of coiling surgical sutures.

According to this invention, the dispenser (1) comprises first and second panels (2,3) joined to each other so as to retain, in a central position, a needle (5) secured to an end of a suture (4), characterized in that the free end of the suture (4) is fixed in co-operation with at least one of the panels (2,3), in a position away from the needle (5).

Further according to the invention, a coiling method is provided for coiling a surgical suture (4) in a dispenser (1) substantially as defined in claim 1, characterized by comprising a step of pulling the free end of the suture (4) in a direction away from the first panel (2).

2 Claims, 3 Drawing Sheets

SURGICAL SUTURES DISPENSER AND A METHOD OF COILING SURGICAL SUTURES

FIELD OF THE INVENTION

The present invention refers to a surgical suture dispenser especially suitable for retaining prepared sutures, that is to say, sutures provided with one or more needles, which are spirally coiled in the dispenser, so that the respective suture (s) will be accessible by its central portion. This invention further relates to a method of coiling surgical sutures.

BACKGROUND OF THE INVENTION

At present, surgeons have a variety of sutures to choose from. Not only traditional materials such as tripes, but also more modern materials—for instance, absorbable sutures— are available in a wide variety of sizes, and a pre-cut stretch of suture material is typically steadied by compression onto a needle to create a prepared suture. Several prepared sutures are generally provided as part of a dispenser kept in a sterilised package, which is opened during surgery to expose a dispenser containing one or more prepared sutures.

It is necessary to retain the needles in a firm and easy-to-release way, so that the needle-holder can be prepared and passed on to the surgeon. The place where the needle is retained in the dispenser is generally referred to as a "needle support". The removal of the needle and the use of the suture should not be prevented either by the needle support or by the way of retaining the suture material in the dispenser.

In addition, the dispenser should not allow the suture material to remain either twisted or folded.

Various types of suture dispensers are known, many of which are individually patented, and the prior art more pertinent to the invention is described in the Brazilian patent application PI 9501435-7. According to this document, a suture dispenser is provided which has two substantially rectangular panels, made of a rigid material. Such panels are centrally aperture, one of them comprising a needle support arranged so that the needle will be accessible through the central openings. The suture is arranged into a flat coil between said panels, so that each loop of the coil will be concentrically arranged around the next one.

The position of the free end of the suture is very important and should be carefully selected, in order to avoid formation of a knot when the suture is being taken out of the dispenser. According to document PI 9501435-7, this free end is secured to the upper panel of the dispenser in a slot made in its larger side. However, this way of securing the free end of the suture causes a number of drawbacks due to its proximity to the central portion of the dispenser, thus favouring the formation of a knot in the suture when the latter is taken out. Besides, securing the free end of the suture in the described position makes the automation of the process difficult, which is vital to guarantee reasonable production costs.

OBJECTIVES OF THE INVENTION

The main objective of the present invention is to provide a surgical suture dispenser which will ensure the removal of a suture without forming knots. Another objective is to provide a suture dispenser the various manufacturing steps of which can be easily automated. In addition, this invention proposes a method of coiling surgical sutures which enables suture dispensers to have the above advantages over those of the prior art.

SUMMARY OF THE INVENTION

A package for a surgical needle and surgical suture wherein the suture has a proximal end and a distal end and the proximal end is mounted to the surgical need. The package has a top panel and a bottom panel. The suture is mounted in the package by coiling the suture on the bottom panel. The distal end of the suture is retained in the bottom panel

DETAILED DESCRIPTION OF THE INVENTION

The present invention will now be described in detail with reference to a preferred embodiment illustrated in the accompanying drawings, in which.

Figure 1:
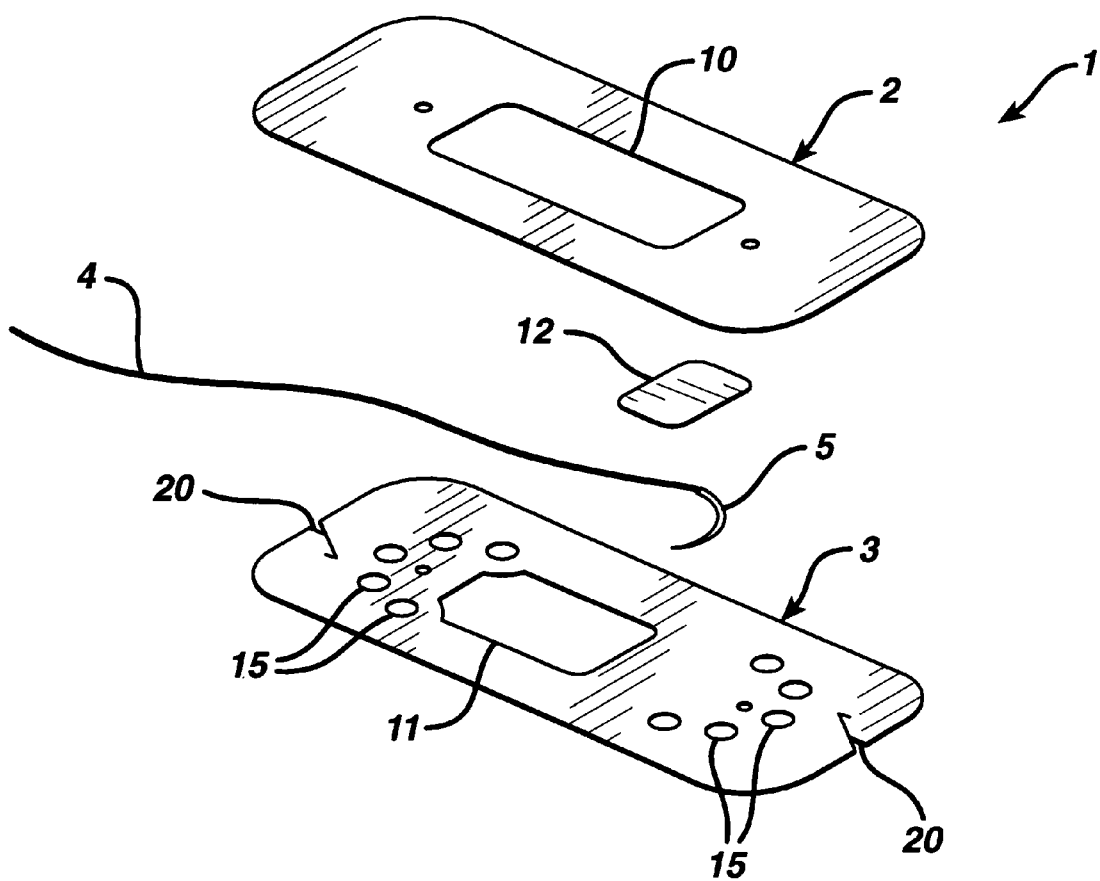
FIG. 1 is an exploded perspective view of a preferred embodiment of the surgical suture dispenser, made in accordance with the teachings of the present invention.

As shown in FIG. 1, the surgical suture dispenser 1 comprises first and second panels 2,3, made of a substantially rigid material such as a plastic or cardboard film, between which a suture 4 provided with at least one needle 5 in one of its ends is arranged.

The panels 3,4 have respective central openings 10,11, which provide access to the needle 5. Such openings 10,11 do not necessarily coincide when the panels are arranged adjacent to each other to form the dispenser 1.

One of said openings can be larger than the other, or otherwise positioned with respect to each other, so that, when the dispenser 1 is assembled, part of the surface of the panels 3,4 can extend through one of the openings 10,11.

The panels 3,4 are substantially rectangular and preferably joined to each other by means of a heatsealing process, which comprises a step of adding an adhesive material to the corresponding face of one of the panels, then applying heat and pressure onto the adhesion points at predetermined periods. The above-mentioned adhesive material includes a thermosensitive film which can be a varnish, a polyethylene film, among others.

The dispenser 1 further comprises a needle support 12 capable of retaining a needle 5 in a position adjacent the openings 10,11. According to a preferred embodiment, the needle support 12 is formed from a self-adhering film which adheres both to the second panel 4 and to the needle 5, thus preventing the needle 5 from coming out of the desired position. This film can be made of paper, a plastic film, non woven materials, etc.

The needle support 12 can also be made from a heatsealing film, which is positioned on the needle assembly 5—second panel 3, being pressed by a heated matrix (not shown) having an adequate shape, which not only causes the film to melt, but also cuts the excess material. In this way, the heatsealing film conforms to the needle 5, fixing it to the panel 3. In addition, the needle support 12 can be made of a foam (not shown) having adhesive at the base and a cut where the needle 5 is fixed. The foam can be made of latex, polyurethane, polyethylene, etc.

Figure 2:
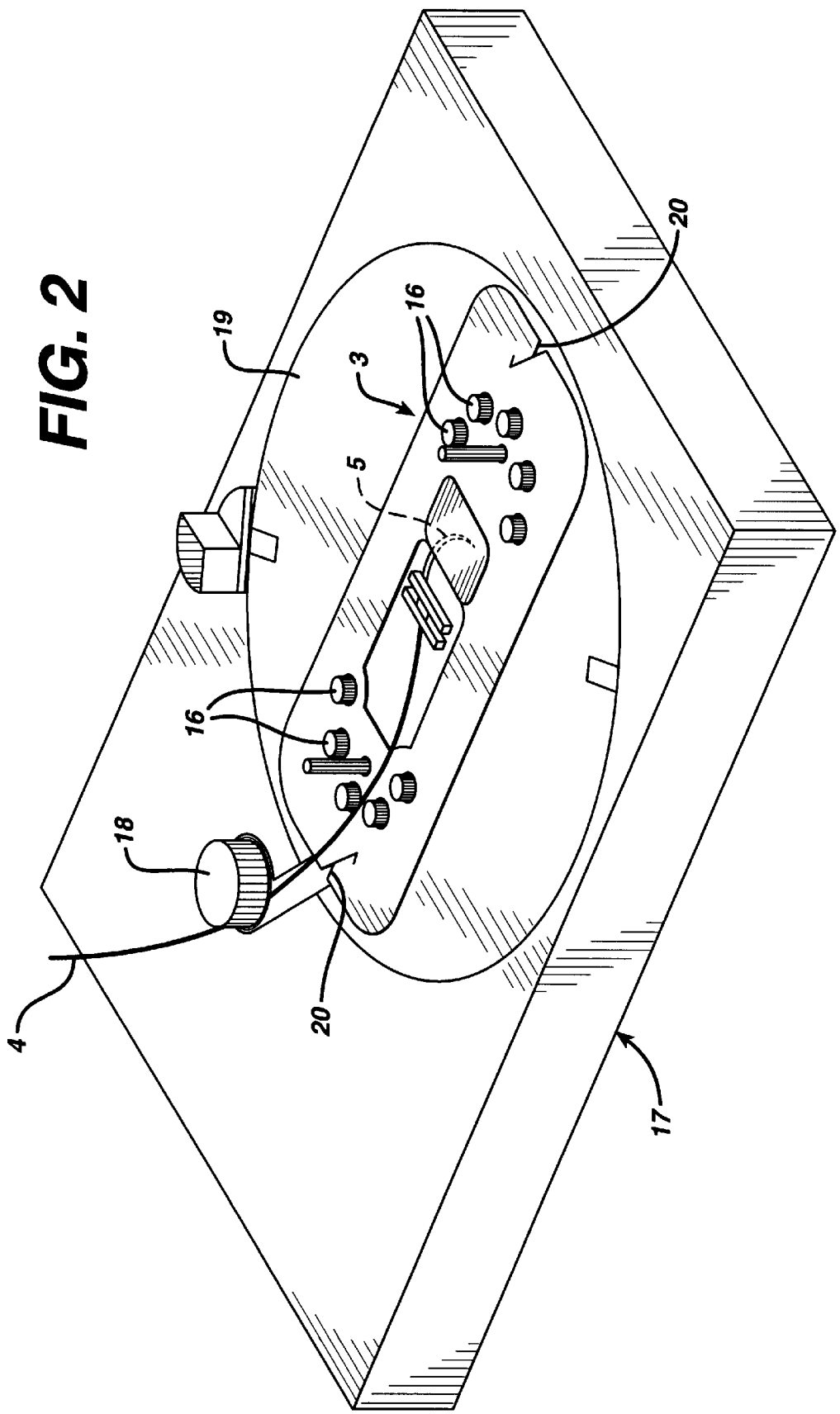
FIG. 2 is a perspective view of a suture-coiling apparatus with a second panel of the surgical suture dispenser illustrated in FIG. 1, at an initial phase of the suture-coiling process.
Figure 3:
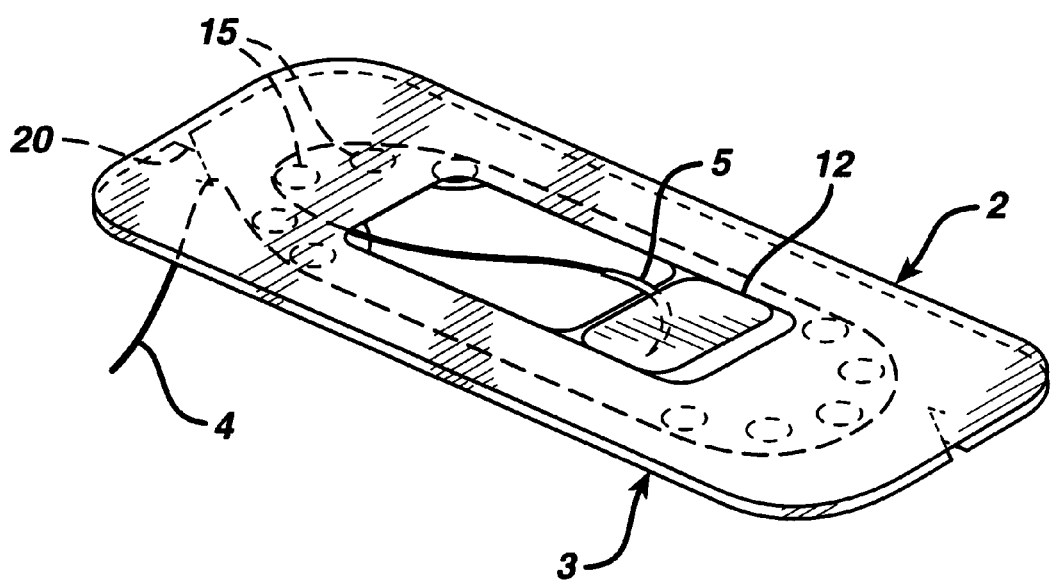
FIG. 3 is a perspective view of the suture-coiling apparatus with the surgical suture dispenser illustrated in FIG. 1, at a final phase of the suture-coiling process.

With reference also to FIG. 2, bores 15 are provided in the panel 3, which are adapted to co-operate with vertical mounting pins 16 of a suture-coiling apparatus 17. As illustrated in detail in FIG. 2 and as known from the prior art, the pins 16 are introduced into the bores 15 at the beginning of the step of coiling the suture 4, in order to form fixed points which define the position of the loops of the suture 4. By securing a determined point of the suture 4 to the jaw 18, and then turning the table 19, the suture 4 will coil around the mounting pins 16, the latter being withdrawn from below at the appropriate moment. The first panel 2 is then secured to the second panel 3, retaining the loops of the suture 4 in a spiral position, which minimize the chances of forming knots when the needle 5 is taken out (see FIG. 3).

According to the specific teachings of the present invention, fixation slots 20 are provided in the smaller sides of the panel 3, the free end of the suture 4 being secured to one of these slots after the coiling process has been completed. As shown specifically in FIG. 3, and also according to the teachings of this invention, the free end of the suture 4 is pulled downwards, after said coiling process has been completed, in a direction away from the first panel 2, the suture being cut at an adequate point. Alternatively, the free end of the suture 4 can be withdrawn under pressure between the panels 2,3.

One should bear in mind that the dispenser and the suture-coiling method described above are only preferred embodiments of the present invention, the scope of which is defined solely by the accompanying claims.

What is claimed is:

1. The combination comprising a surgical suture dispenser (1) especially suitable for retaining sutures provided with one or more needles, and a surgical needle having a end and a suture having a proximal end and a distal end, wherein the proximal end of the suture is mounted to the needle, said dispenser comprising first and second panels (2,3) each having a top and a bottom joined to each other so as to retain, in a central position, the needle (5) and suture (4), characterized in that the distal end of the suture (4) is secured in co-operation with the second panel (3) in a position away from the needle (5);

wherein the panels (2,3) are substantially rectangular, with securing slots (20) being provided in the smaller sides of the second panel (3), which cooperates with the free end of the suture (4);

wherein a needle support (12) is provided on the second panel (3), for securing the needle (5) to said panel (3);

wherein respective central openings (10,11) are provided in the panels (2,3)

wherein the suture is coiled onto the top of second panel (3), and the distal end of the suture is retained in the securing slot (20) in second panel (3).

2. A method of winding a surgical suture having an attached surgical needle into a package, said method comprising the steps of:

providing a surgical needle having a suture having a proximal end and a distal end, wherein the proximal end of the suture is mounted to the needle;

providing a package comprising:

a surgical suture dispenser (1) especially suitable for retaining sutures provided with one or more needles, said dispenser comprising first and second panels (2,3) each having a top and a bottom joined to each other so as to retain, in a central position, the needle and a suture (4), characterized in that the distal end of the suture (4) is secured in co-operation with the second panel (3), in a position away from the needle (5);

wherein the panels (2,3) are substantially rectangular, with securing slots (20) being provided in the smaller sides of the second panel (3), which cooperates with the free end of the suture (4);

wherein a needle support (12) is provided on the second panel (3), for securing the needle (5) to said panel (3); and, wherein respective central openings (10,11) are provided in the panels (2,3); and, then coiling the suture onto the top of second panel (3), and retaining the distal end of the suture in the securing slot (20) in second panel (3).

* * * * *